United States Patent
Arimoto

(10) Patent No.: US 9,372,169 B2
(45) Date of Patent: Jun. 21, 2016

(54) METHOD FOR ACCURATELY QUANTIFYING A CHEMICAL SUBSTANCE CONTAINED IN A SAMPLE SOLUTION AT A SIGNIFICANTLY LOW CONCENTRATION OF NOT MORE THAN 1×10−8M

(71) Applicant: PANASONIC CORPORATION, Osaka (JP)

(72) Inventor: Satoshi Arimoto, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 501 days.

(21) Appl. No.: 13/910,601

(22) Filed: Jun. 5, 2013

(65) Prior Publication Data

US 2014/0021068 A1    Jan. 23, 2014

(30) Foreign Application Priority Data

Jul. 20, 2012   (JP) .................... 2012-161178

(51) Int. Cl.
*G01N 27/327*  (2006.01)
*G01N 27/333*  (2006.01)
*G01N 27/406*  (2006.01)

(52) U.S. Cl.
CPC ............ *G01N 27/406* (2013.01); *G01N 27/327* (2013.01); *G01N 27/3277* (2013.01); *G01N 27/333* (2013.01)

(58) Field of Classification Search
CPC ..... G01N 27/48; G01N 27/49; G01N 27/423; G01N 27/327–27/3272
See application file for complete search history.

(56) References Cited

U.S. PATENT DOCUMENTS

| | | | | |
|---|---|---|---|---|
| 5,389,215 A | * | 2/1995 | Horiuchi | ................ G01N 27/42 204/412 |
| 2009/0283404 A1 | | 11/2009 | Kakiuchi et al. | |
| 2012/0216604 A1 | | 8/2012 | Arimoto | |

FOREIGN PATENT DOCUMENTS

| | | |
|---|---|---|
| EP | 0569908 A2 | 11/1993 |
| EP | 0569908 A3 | 11/1993 |

(Continued)

OTHER PUBLICATIONS

Ohtani et al., "Differential pulse stripping voltammetry of moderately hydrophobic ions based on hydrophobic ionic liquid membranes supported on the Ag/AgCl electrode," Journal of Electroanalytical Chemistry 656 (2011) 102-105.*

*Primary Examiner* — Alexander Noguerola
(74) *Attorney, Agent, or Firm* — McDermott Will & Emery LLP

(57) ABSTRACT

Provided is a method for accurately quantifying a chemical substance contained in a sample solution at a significantly low concentration of not more than $1 \times 10^{-8}$M. A measurement system used for the method includes a counter electrode 13, a first reference electrode 12, a first working electrode 11a, a second working electrode 11b, a second reference electrode 14 and a gel-coated electrode 15. The gel-coated electrode 15 is electrically equivalent to the second working electrode 11b. The gel-coated electrode 15 comprises an electrode body 31 and a gel 34. The surface of the electrode body 31 is coated with the gel 34. The gel 34 contains a standard electrolyte and an ionic liquid. The gel 34 contains no water. The ionic liquid is hydrophobic and nonvolatile. The ionic liquid is composed of a cation and an anion. The standard electrolyte is composed of the cation and a halide ion.

18 Claims, 7 Drawing Sheets

(56) References Cited

FOREIGN PATENT DOCUMENTS

| | | | |
|---|---|---|---|
| EP | 0569908 | B1 | 11/1993 |
| JP | 06-027081 | A | 2/1994 |
| JP | 2007-255906 | A | 10/2007 |
| JP | 2010-286423 | A | 12/2010 |
| JP | 2011-058900 | A | 3/2011 |
| JP | 4991967 | B1 | 8/2012 |
| WO | 2008-032790 | A1 | 3/2008 |

* cited by examiner

METHOD FOR ACCURATELY QUANTIFYING A CHEMICAL SUBSTANCE CONTAINED IN A SAMPLE SOLUTION AT A SIGNIFICANTLY LOW CONCENTRATION OF NOT MORE THAN 1×10−8M

RELATED APPLICATIONS

This application claims the benefit of Japanese Application No. 2012-161178, filed on Jul. 20, 2012, the disclosure of which Application is incorporated by reference herein.

BACKGROUND OF THE INVENTION

1. Field of the Invention

The present invention relates to a method for accurately quantifying a chemical substance contained in a sample solution at a significantly low concentration of not more than $1\times10^{-8}$M.

2. Description of the Related Art

Japanese Patent Laid-Open Publication No. 2010-286423 discloses a method for quantifying a chemical substance contained in a sample solution by a potentiometric method. In the potentiometric method, a surface potential of a measurement electrode which varies with a chemical reaction is measured.

SUMMARY OF THE INVENTION

The purpose of the present invention is to provide a method for accurately quantifying a chemical substance contained in a sample solution at a significantly low concentration of not more than $1\times10^{-8}$M.

The present invention is a method for accurately quantifying a chemical substance contained in a sample solution at a significantly low concentration of not more than $1\times10^{-8}$M, the method comprising steps of:

(a) preparing a measurement system including a counter electrode, a first reference electrode, a first working electrode, a second working electrode, a second reference electrode and a gel-coated electrode; wherein the gel-coated electrode is electrically equivalent to the second working electrode;

the gel-coated electrode comprises an electrode body and a gel;

the surface of the electrode body is coated with the gel;

the gel contains a standard electrolyte and an ionic liquid;

the gel contains no water;

the ionic liquid is hydrophobic and nonvolatile;

the ionic liquid is composed of a cation and an anion; and the standard electrolyte is composed of the cation and a halide ion;

(b) bringing the counter electrode, the first reference electrode, the first working electrode, the second working electrode, the second reference electrode and the gel-coated electrode into contact with the sample solution; wherein the sample solution contains the chemical substance and an oxidation-reduction substance or contains the chemical substance modified with an oxidation-reduction substance;

(c) applying voltages of V1 volts and V2 volts (V1>V2) to the first working electrode and the second working electrode, respectively, for a first predetermined period t1 with use of a potentiostat 18 so as to develop chemical reactions represented by the following chemical formulae (I) and (II) on the surfaces of the first working electrode and the second working electrode, respectively;

On the first working electrode:

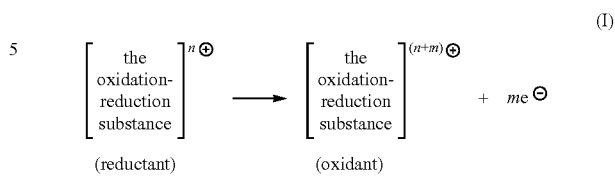

(where, n represents an integer, and m represents a positive integer)

On the second working electrode:

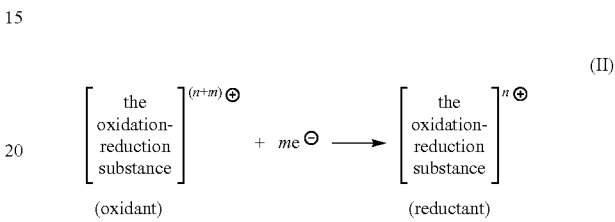

(where, n represents an integer, and m represents a positive integer)

(d) stopping the application of the voltage to the second working electrode and the gel-coated electrode, when the first predetermined period t1 elapses;

(e) leaving the sample solution as it stands for a second predetermined period t2 after the step (d);

(f) measuring a voltage difference ΔE between the second working electrode and the second reference electrode after the step (e); and (g) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant
C2: constant.

The another present invention is a method for accurately quantifying a chemical substance contained in a sample solution at a significantly low concentration of not more than $1\times10^{-8}$M, the method comprising steps of:

(a) preparing a measurement system including a counter electrode, a first reference electrode, a first working electrode, a second working electrode, a second reference electrode and a gel-coated electrode; wherein the gel-coated electrode is electrically equivalent to the second working electrode;

the gel-coated electrode comprises an electrode body and a gel;

the surface of the electrode body is coated with the gel;

the gel contains a standard electrolyte and an ionic liquid;

the gel contains no water;

the ionic liquid is hydrophobic and nonvolatile;

the ionic liquid is composed of a cation and an anion; and the standard electrolyte is composed of the cation and a halide ion;

(b) bringing the counter electrode, the first reference electrode, the first working electrode, the second working electrode and the gel-coated electrode into contact with the sample solution; wherein the sample solution contains the chemical substance and an oxidation-reduction substance or contains the chemical substance modified with an oxidation-reduction substance; and the second reference electrode is not in contact with the sample solution;

(c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode and the second working electrode, respectively;

On the first working electrode:

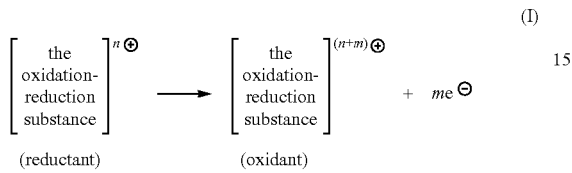
(I)

(where, n represents an integer, and m represents a positive integer)

On the second working electrode:

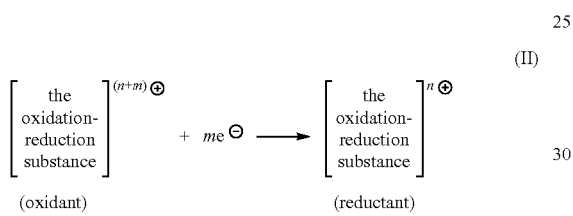
(II)

(where, n represents an integer, and m represents a positive integer)

(d) stopping the application of the voltage to the second working electrode and the gel-coated electrode when the first predetermined period elapses;

(e) leaving the sample solution as it stands for a second predetermined period t2 after the step (d);

(f) bringing the second reference electrode into contact with the sample solution;

(g) measuring a voltage difference $\Delta E$ between the second working electrode and the second reference electrode after the step (f); and (h) calculating a concentration of the chemical substance on the basis of the following formula (III)

$$\Delta E = C1 \cdot \log_{10}(\text{the concentration of the chemical substance}) + C2 \quad \text{(III)}$$

C1: proportional constant
C2: constant.

The voltage difference between the voltages of V1 and V2 in the step (c) may be not less than 0.3 volts and not more than 0.6 volts.

The first predetermined period t1 may be not less than 10 seconds and not more than 600 seconds.

The second predetermined period t2 may be not less than 10 seconds and not more than 600 seconds.

The oxidation-reduction substance may be a ferrocene derivative.

The ferrocene derivative may be ferrocenecarboxylic acid.

The chemical substance may be an antibody.

The cation and the anion may be selected from the following groups (I) and (II), respectively:

Group (I): cations represented by the following formulae IV-(1) to IV-(6).

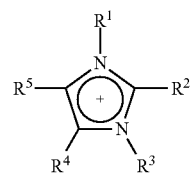

imidazolium ion
IV-(1)

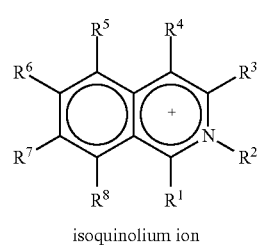

isoquinolium ion
IV-(2)

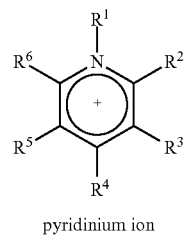

pyridinium ion
IV-(3)

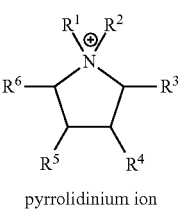

pyrrolidinium ion
IV-(4)

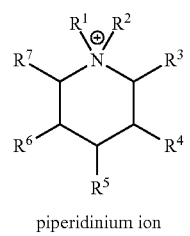

piperidinium ion
IV-(5)

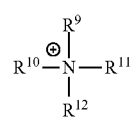

ammonium ion
IV-(6)

(where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may include a heteroatom, an aralkyl group, or an aryl group.)

Group (II): anions represented by the following formulae V-(1) and V-(2).

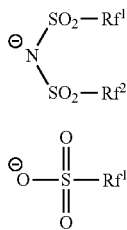

(where $Rf^1$ and $Rf^2$ are the same as or different from each other, and each represents a perfluoroalkyl group having carbon number of 1 to 4.)

The ionic liquid may be selected from the following:

1,3-dimethylimidazolium bis(trifluoromethanesulfonyl)imide, 1-ethyl-3-methylimidazolium bis(trifluoromethanesulfonyl)imide, 1-ethyl-3-methylimidazolium triflate, 1-ethyl-3-methylimidazolium bis(pentafluoroethanesulfonyl)imide, 1,3-diethylimidazolium bis(trifluoromethanesulfonyl)imide, 1,3-diethylimidazolium triflate, 1-butyl-3-ethylimidazolium triflate, 1,2-dimethyl-3-ethylimidazolium bis(trifluoromethanesulfonyl)imide, 1-butyl-3-methylimidazolium bis(trifluoromethanesulfonyl)imide, 1-butyl-3-methylimidazolium triflate, 1-isopropyl-3-methylimidazolium bis(trifluoromethanesulfonyl)imide, 1,2-dimethyl-3-propylimidazolium bis(trifluoromethanesulfonyl)imide, N,N-propylmethylpyrrolidinium bis(trifluoromethanesulfonyl)imide, propyltrimethylammonium bis(trifluoromethanesulfonyl)imide, N,N-methylpropylpiperidinium bis(trifluoromethanesulfonyl)imide, and N-butylpyridinium bis(trifluoromethanesulfonyl)imide.

The present invention provides a method for accurately quantifying a chemical substance contained in a sample solution at a significantly low concentration of not more than $1 \times 10^{-8}$ M.

Other features, elements, processes, steps, characteristics and advantages of the present invention will become more apparent from the following detailed description of preferred embodiments of the present invention with reference to the attached drawings.

DETAILED DESCRIPTION OF THE INVENTION

The embodiments of the present invention are described below.

(Embodiment 1)

(Step (a))

Figure 1A:
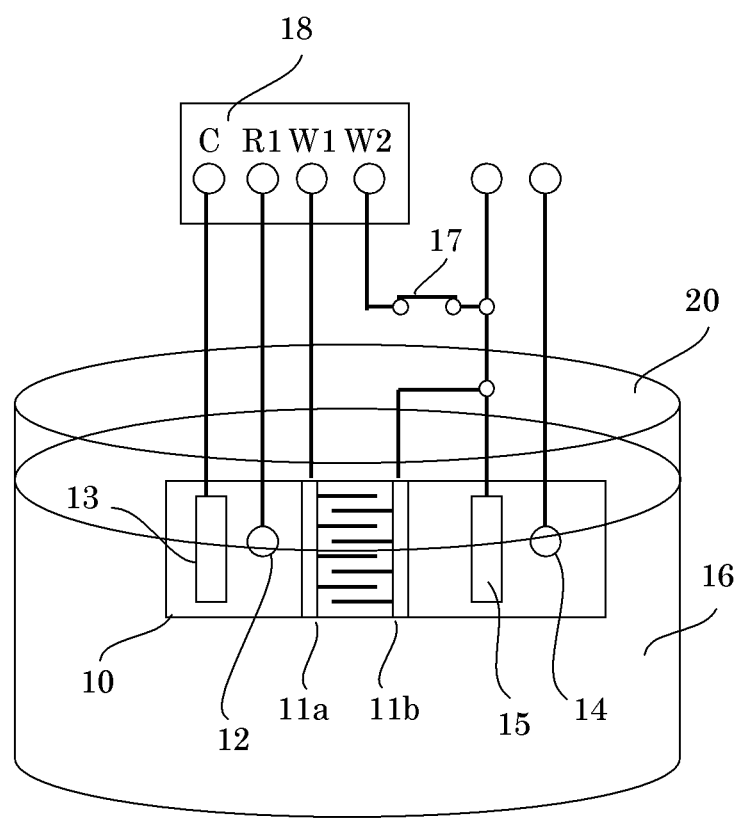
FIG. 1A schematically shows the step (a)-step (c) in the embodiment 1.

FIG. 1A shows a measurement system used in the embodiment 1. The measurement system includes a counter electrode 13, a first reference electrode 12, a first working electrode 11a, a second working electrode 11b, a second reference electrode 14 and a gel-coated electrode 15. The counter electrode 13, the first reference electrode 12, the first working electrode 11a, the second working electrode 11b and the gel-coated electrode 15 are connected to a potentiostat 18. A switch 17 is provided between the potentiostat 18 and the second working electrode 11b. In the step (b) and the step (c), the switch 17 is kept on.

It is desirable that the first working electrode 11a and the second working electrode 11b are comb-shaped electrodes. It is desirable that these two comb-shaped electrodes are engaged alternately.

An example of the counter electrode 13 is a palladium electrode. An example of the first reference electrode 12 is a silver/silver chloride electrode.

An example of the first working electrode 11a is a gold electrode. An example of the second working electrode 11b is also a gold electrode. It is desirable that the gold electrode is covered with a self-assembled film composed of alkanethiol. It is desirable that the first working electrode 11a and the second working electrode 11b are composed of a pair of identical electrodes.

Figure 3A:
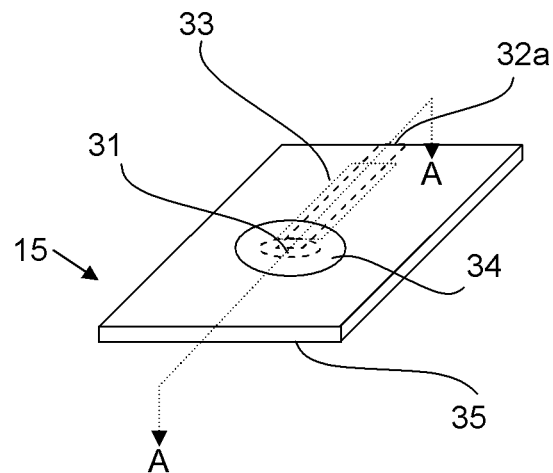
FIG. 3A schematically shows an embodiment of a gel-coated electrode 15.
Figure 3B:
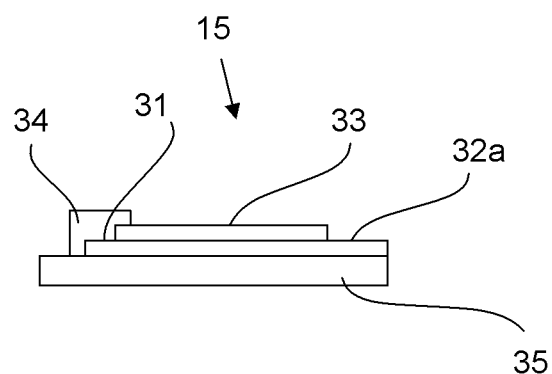
FIG. 3B shows a cross-sectional view of the A-A line included in FIG. 3A.

As shown in FIG. 3A, the gel-coated electrode 15 comprises an electrode body 31 and a gel 34. The electrode body 31 is coated with the gel 34. In more detail, the gel-coated electrode 15 comprises an electrically conductive line 32a, an insulating layer 33 and an insulating substrate 35. As shown in FIG. 3B, the electrically conductive line 32a is interposed between the insulating layer 33 and the insulating substrate 35. Desirably, the electrically conductive line 32a is formed of silver.

The main portion of the electrically conductive line 32a is coated with the insulating layer 33. However, one end of the electrically conductive line 32a is not coated with the insulating layer 33. The one end of the electrically conductive line 32a is coated with the gel 34. In other words, the one end of the electrically conductive line 32a is the electrode body 31. The other end of the electrically conductive line 32a is not coated with the insulating layer 33, either. The other end of the electrically conductive line 32a is used to connect the electrode body 31 to the potentiostat 18 electrically.

Figure 3C:
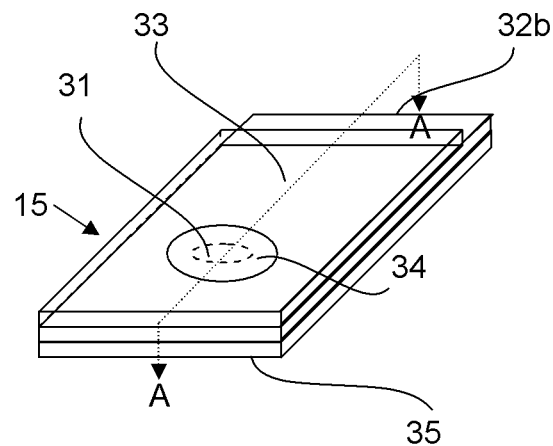
FIG. 3C schematically shows another embodiment of the gel-coated electrode 15.
Figure 3D:
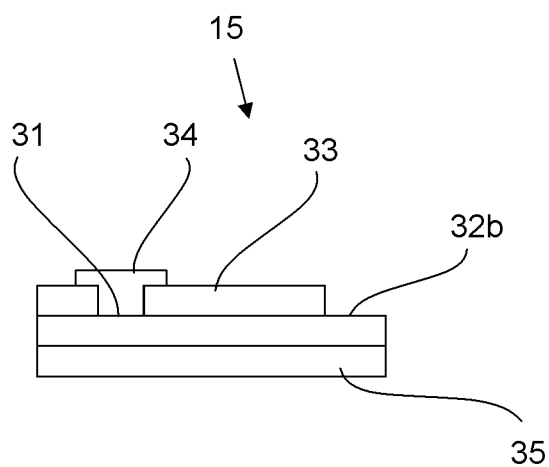
FIG. 3D shows a cross-sectional view of the A-A line included in FIG. 3C.

FIG. 3C shows another embodiment of the gel-coated electrode 15. The gel-coated electrode shown in FIG. 3C comprises an electrically conductive plate 32b, the insulating layer 33, the gel 34 and the insulating substrate 35. Desirably, the electrically conductive plate 32b is formed of silver. As shown in FIG. 3D, the electrically conductive plate 32b is interposed between the insulating layer 33 and the insulating substrate 35. An opening is provided in the insulating layer 33. The gel 34 is provided in the opening in such a manner that the gel 34 is in contact with the electrically conductive plate 32b. The portion of the electrically conductive plate 32b which is in contact with the gel 34 is the electrode body 31. In this way, the electrode body 31 is coated with the gel 34.

The electrically conductive plate 32b is surrounded by an insulating material (not shown). The portion of the electrically conductive plate 32b which is coated neither with the gel 34 nor with the insulating layer 33 is used to connect the electrode body 31 to the potentiostat 18 electrically.

Next, the gel 34 is described below in more detail.

The gel 34 contains the standard electrolyte and the ionic liquid. The ionic liquid serves as a support electrolyte. The gel 34 is configured so that the standard electrolyte and the ionic liquid are not mixed with the sample solution. A method for configuring the gel 34 is not limited. An example is to support and/or include the standard electrolyte and the ionic liquid in a hydrophobic polymer. An example of the hydrophobic polymer is (vinylidene fluoride-hexafluoropropylene) copolymer, polymethyl methacrylate, polyacrylonitrile, or polybutylacrylate.

The ionic liquid is hydrophobic. The hydrophobic ionic liquid is composed of the following cation and anion.

Cation: cations represented by the following formulae IV-(1) to IV-(6).

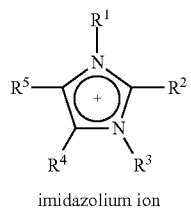
imidazolium ion
IV-(1)

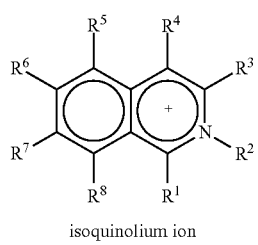
isoquinolium ion
IV-(2)

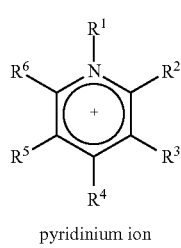
pyridinium ion
IV-(3)

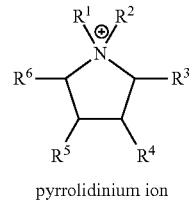
pyrrolidinium ion
IV-(4)

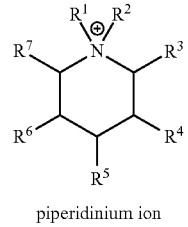
piperidinium ion
IV-(5)

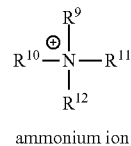
ammonium ion
IV-(6)

(where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may included a heteroatom, an aralkyl group, or an aryl group.)

Preferably, in the imidazolium ion represented by the formula IV-(1), $R^1$ is selected from the group consisting of a methyl group, a ethyl group, an n-propyl group, an isopropyl group, an n-butyl group, an isobutyl group, and a t-butyl group, $R^2$ is a hydrogen atom or a methyl group, $R^3$ is an alkyl group having carbon number of 1 to 6 which may include a hetero atom, and $R^4$ and $R^5$ are hydrogen atoms.

Preferably, in the isoquinolium ion represented by the formula IV-(2), $R^2$ is an alkyl group having carbon number of 1 to 6 which may include a hetero atom, and $R^1$, $R^3$, $R^4$, $R^5$, $R^6$, $R^7$, and $R^8$ are hydrogen atoms.

Preferably, in the pyridinium ion represented by the formula IV-(3), $R^1$ is an alkyl group having carbon number of 1 to 6 which may include a hetero atom, and $R^2$, $R^3$, $R^4$, $R^5$, and $R^6$ are hydrogen atoms.

Preferably, in the pyrrolidinium ion represented by the formula IV-(4), $R^1$ is selected from the group consisting of methyl group, ethyl group, n-propyl group, isopropyl group, n-butyl group, isobutyl group, and t-butyl group, $R^2$ is an alkyl group having carbon number of 1 to 6 which may contain hetero atom, $R^3$, $R^4$, $R^5$, and $R^6$ are hydrogen atom.

Preferably, in the piperidinium ion represented by the formula IV-(5), $R^1$ is selected from the group consisting of a methyl group, an ethyl group, an n-propyl group, an isopropyl group, an n-butyl group, an isobutyl group, and a t-butyl group, $R^2$ is an alkyl group having carbon number of 1 to 6 which may include a hetero atom, and $R^3$, $R^4$, $R^5$, $R^6$, and $R^7$ are hydrogen atoms.

Preferably, in the ammonium ion represented by the formula IV-(6), $R^9$, $R^{10}$, $R^{11}$, and $R^{12}$ are the same as or different from each other, and each represent an alkyl group having carbon number of 1 to 6 which may include a halogen atom, a phenyl group, or a benzyl group.

Anion: anions represented by the following formula V-(1) and V-(2).

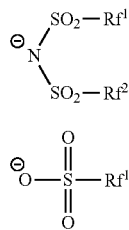

(where $Rf^1$ and $Rf^2$ are the same as or different from each other, and each represents a perfluoroalkyl group having carbon number of 1 to 4.)

Preferably, in the anion represented by the formula V-(1), both $Rf^1$ and $Rf^2$ are perfluoromethyl groups or perfluoroethyl groups.

Preferably, in the anion represented by the formula V-(2), $Rf^1$ is a trifluoromethyl group.

More specifically, the ionic liquid is exemplified below.
1,3-dimethylimidazolium bis(trifluoromethanesulfonyl)imide
1-ethyl-3-methylimidazolium bis(trifluoromethanesulfonyl)imide
1-ethyl-3-methylimidazolium triflate
1-ethyl-3-methylimidazolium bis(pentafluoroethanesulfonyl)imide
1,3-diethylimidazolium bis(trifluoromethanesulfonyl)imide
1,3-diethylimidazolium triflate
1-butyl-3-ethylimidazolium triflate
1,2-dimethyl-3-ethylimidazolium bis(trifluoromethanesulfonyl)imide
1-butyl-3-methylimidazolium bis(trifluoromethanesulfonyl)imide
1-butyl-3-methylimidazolium triflate
1-isopropyl-3-methylimidazolium bis(trifluoromethanesulfonyl)imide
1,2-dimethyl-3-propylimidazolium bis(trifluoromethanesulfonyl)imide
N,N-propylmethylpyrrolidinium bis(trifluoromethanesulfonyl)imide
propyltrimethyammonium bis(trifluoromethanesulfonyl)imide
N,N-methylpropylpiperidinium bis(trifluoromethanesulfonyl)imide
N-butylpyridinium bis(trifluoromethanesulfonyl)imide The standard electrolyte is composed of the above-mentioned cation and a halide ion. The halide ion denotes a chloride ion, a bromide ion, or an iodide ion.

It is preferred that the standard electrolyte includes identical or similar cation to that of the ionic liquid in light of solubility. The "similar cation" means any cation represented by the formula IV-(1), when the cation of the ionic liquid is a cation represented by the formula IV-(1). Specifically, when the ionic liquid is 1-butyl-3-methylimidazolium bis(trifluoromethanesulfonyl)imide, the standard electrolyte is preferably 1-butyl-3-methylimidazolium halide. More preferably, the standard electrolyte may be 1-butyl-3-methylimidazolium chloride.

The gel-coated electrode 15 is electrically equivalent to the second working electrode 11b. The term "electrically equivalent" means that the gel-coated electrode 15 is connected directly and electrically to the second working electrode 11b and that a resistor, a capacitor or a coil is not located electrically between the gel-coated electrode 15 and the second working electrode 11b. As shown in FIG. 1A, it is desirable that the gel-coated electrode 15 is connected to the second working electrode 11b with use of an electric line.

(Step (b))

Figure 1B:
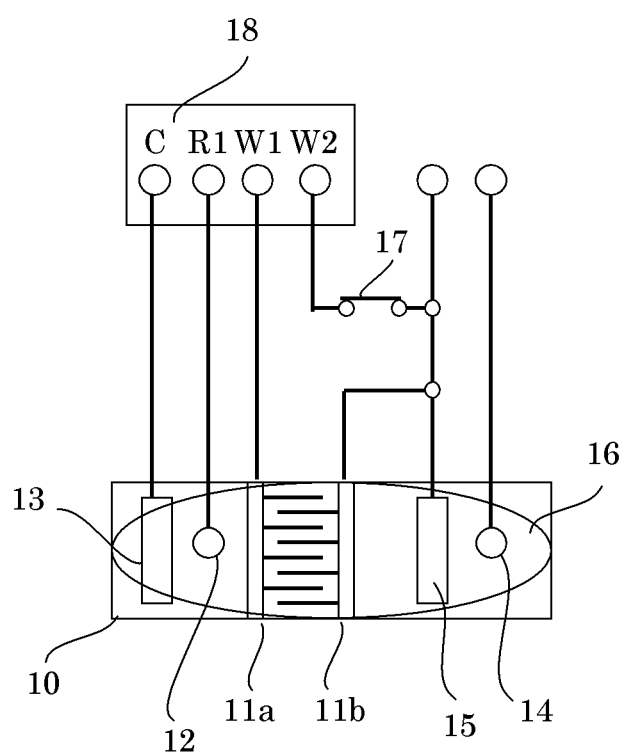
FIG. 1B schematically shows the step (a)-step (c) in the embodiment 1.

The step (b) is performed after the step (a). In the step (b), the counter electrode 13, the first reference electrode 12, the first working electrode 11a, the second working electrode 11b, the second reference electrode 14 and the gel-coated electrode 15 are brought into contact with the sample solution 16. More particularly, as shown in FIG. 1B, the sample solution 16 is dropped onto a substrate 10 in such a manner that the sample solution 16 covers the counter electrode 13, the first reference electrode 12, the first working electrode 11a, the second working electrode 11b, the second reference electrode 14 and the gel-coated electrode 15. Instead of this, as shown in FIG. 1A, the counter electrode 13, the first reference electrode 12, the first working electrode 11a, the second working electrode 11b, the second reference electrode 14 and the gel-coated electrode 15 are immersed in the sample solution 16 contained in a vessel 20. It is desirable that the sample solution 16 is an aqueous solution. It is more desirable that the sample solution 16 is a buffer solution.

In FIG. 1A and FIG. 1B, the counter electrode 13, the first reference electrode 12, the first working electrode 11a, the second working electrode 11b, the second reference electrode 14 and the gel-coated electrode 15 are formed on one insulating substrate 10. Accordingly, the sample solution 16 is dropped onto the substrate 10, or the substrate 10 is immersed in the sample solution 16. However, these six electrodes 11-15 may be brought into contact with the sample solution 16 separately without use of the substrate 10.

Here, the chemical substance to be quantified according to the present embodiment is described. The sample solution 16 contains the chemical substance and an oxidation-reduction substance. Instead of this, the sample solution 16 may contain the chemical substance modified with the oxidation-reduction substance. The sample solution 16 contains an antibody modified with ferrocenecarboxylic acid in the example, which is described later.

The oxidation-reduction substance is contained in the sample solution 16 in a state of either oxidant or reductant. The oxidation-reduction substance is changed from the oxidant state to the reductant state or from the reductant state to the oxidant state, when the chemical substance is changed to another chemical substance by the chemical reaction associated with exchange of electrons, namely, the oxidation-reduction reaction.

An example of the chemical substance is a sugar or an antibody. An example of the oxidation-reduction substance is flavin adenine dinucleotide (hereinafter, referred to as "FAD"), potassium ferrocyanide (reductant), potassium ferricyanide (oxidant), ferrocene (and derivatives thereof) or quinone (and the derivative thereof). Generally, the oxidation-reduction substance is called "electron mediator".

Figure 5:
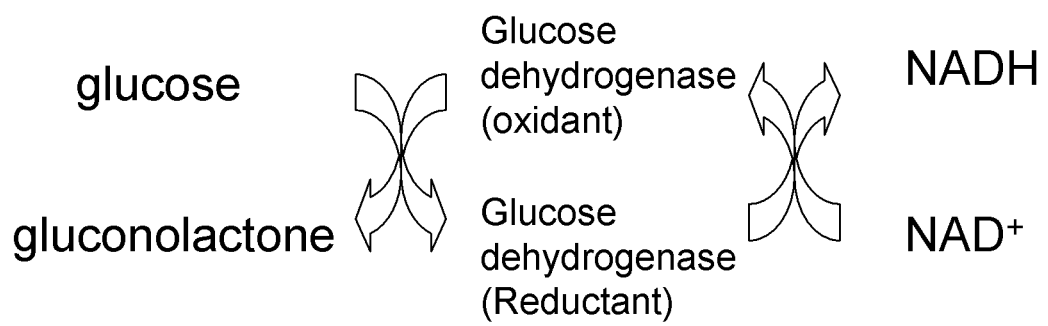
FIG. 5 shows oxidation of glucose by glucose dehydrogenase.

As one example, oxidation of glucose by glucose dehydrogenase is described. As shown in FIG. 5, glucose and nicotinamide adenine dinucleotide are used as the chemical substance and the oxidation-reduction substance, respectively. Glucose is changed to gluconolactone by glucose dehydrogenase. At the same time, the nicotinamide adenine dinucleotide oxidant (hereinafter, referred to as "$NAD^+$") is changed to the reductant thereof (hereinafter, referred to as "NADH").

(Step (c))

The step (c) is performed after the step (b). In the step (c), the voltages of V1 volts and V2 volts (V1>V2) are applied to the first working electrode 11a and the second working electrode 11b, respectively, for a first predetermined period t1 with use of the potentiostat 18. The voltage of V2 volts is also applied to the gel-coated electrode 15. This voltage application develops the chemical reaction represented by the following chemical formula (I) on the surface of the first working electrode 11a.

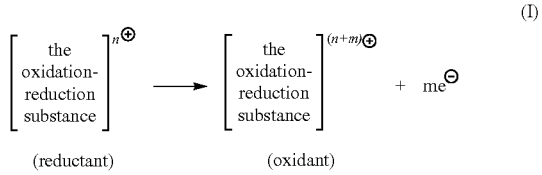

(where, n represents an integer, and m represents a positive integer)

At the same time, the voltage application develops the chemical reaction represented by the following chemical formula (II) on the surface of the second working electrode 11b.

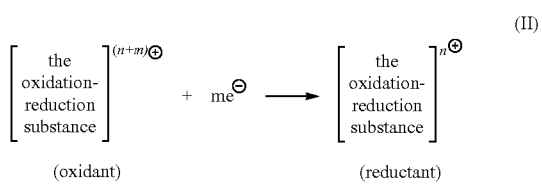

(where, n represents an integer, and m represents a positive integer)

In the step (c), the first working electrode 11a and the second working electrode 11b serve as an anode electrode and a cathode electrode, respectively.

It is desirable that the voltage V1 is not less than 0.3 volts and not more than 0.6 volts. In case where the voltage V1 is less than 0.3 volts, the chemical reaction represented by the chemical formula (I) may not be developed well. In case where the voltage V1 is more than 0.6 volts, an electrolysis reaction of water may be developed.

It is desirable that the voltage V2 is not less than −0.2 volts and not more than 0 volts. In case where the voltage V2 is less than −0.2 volts, an electrolysis reaction of water may be developed. In case where the voltage V2 is more than 0 volts, the chemical reaction represented by the chemical formula (II) may not be developed well.

It is desirable that the voltage difference (V1−V2) is not less than 0.2 volts and not more than 0.8 volts. In case where the voltage difference (V1−V2) is less than 0.2 volts, an oxidation-reduction reaction cycle may not be developed sufficiently. In case where the voltage difference (V1−V2) is more than 0.8 volts, an electrolysis reaction of water may be developed.

As one example, the voltages V1 and V2 are 0.3 volts (vs. the first reference electrode 12) and 0 volts (vs. the first reference electrode 12), respectively.

It is desirable that the first predetermined period t1 is not less than 10 seconds and not more than 600 seconds. In case where the first predetermined period t1 is less than 10 seconds, the chemical reactions represented by the chemical formulae (I) and (II) may not be developed sufficiently. In case where the first predetermined period t1 is more than 600 seconds, the solvent (water) contained in the sample solution 16 may be evaporated to vary the concentration of the sample solution 16. It is desirable that the second reference electrode 14 is in a floating state in the step (c).

(Step (d))

When the first predetermined period t1 elapses, the application of voltage V2 to the second working electrode 11b and the gel-coated electrode 15 is stopped. More particularly, the switch 17 is turned off. When the switch 17 is turned off, the electrical state of the second working electrode 11b and the gel-coated electrode 15 comes into a floating state. It is desirable that the voltage V1 is maintained at the first working electrode 11a in the step (d).

(Step (e))

After the step (d), the step (e) is performed. In the step (e), the sample solution 16 is left as it stands for the second predetermined period t2.

It is desirable that the second predetermined period t2 is not less than 10 seconds and not more than 600 seconds. In case where the second predetermined period t2 is less than 10 seconds, the noise generated by switching in the step (d) may be included erroneously in the voltage difference ΔE, which is described later. In case where the second predetermined period t2 is more than 600 seconds, the solvent (water) contained in the sample solution 16 may be evaporated to vary the concentration of the sample solution 16.

(Step (f))

Figure 2A:
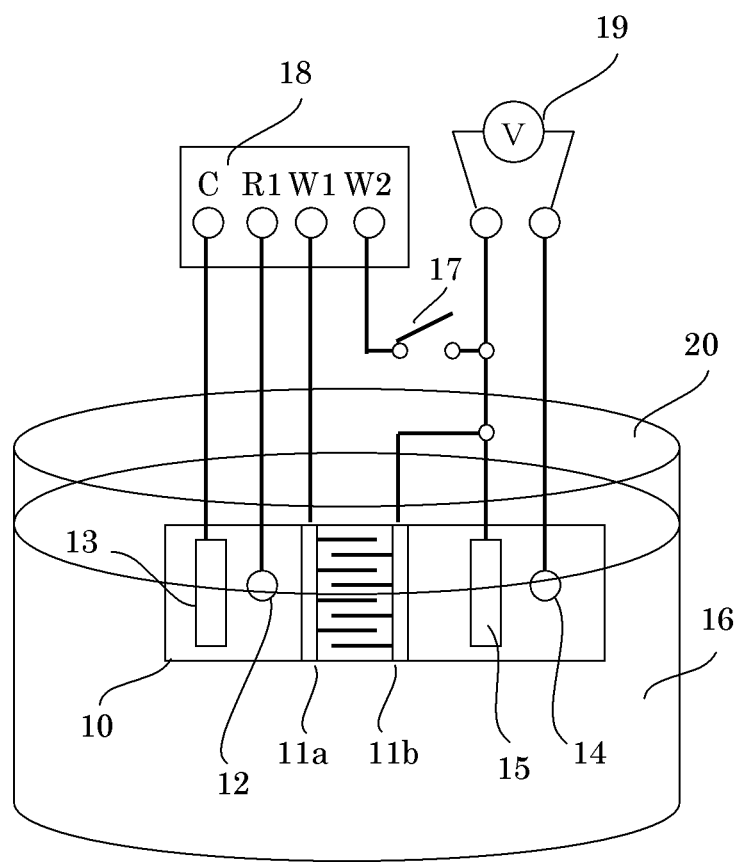
FIG. 2A schematically shows the step (f) in the embodiment 1.
Figure 2B:
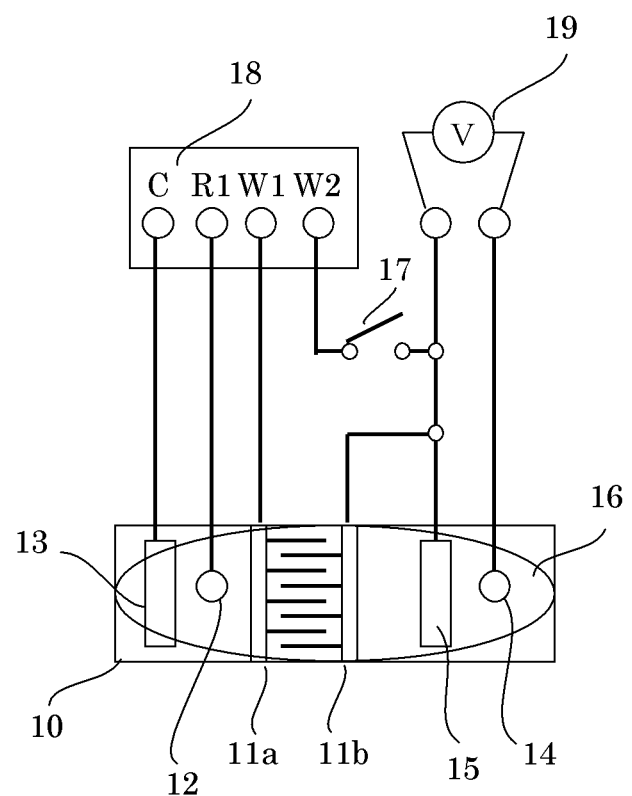
FIG. 2B schematically shows the step (f) in the embodiment 1.

When the second predetermined period t2 elapses, the voltage difference ΔE between the second working electrode 11b and the second reference electrode 14 is measured. More particularly, as shown in FIG. 2A and FIG. 2B, a voltmeter 19 is interposed electrically between the second working electrode 11b and the second reference electrode 14. Needless to say, in the step (f), the second working electrode 11b, the gel-coated electrode 15 and the second reference electrode 14 are in contact with the sample solution 16.

The present inventors have discovered that the voltage difference ΔE is proportional to the concentration of the chemical substance contained in the sample solution 16, even when the chemical substance contained in the sample solution 16 has a significantly low concentration of not more than $1 \times 10^{-8}$M. The present invention is characterized by this discovery. The lower limit of the concentration can be $1 \times 10^{-12}$M.

(Step (g))

Finally, on the basis of the voltage difference ΔE measured in the step (f), the concentration of the chemical substance is calculated in accordance with the following formula (III):

$$\Delta E = C1 \cdot \log_{10}(\text{the concentration of the chemical substance}) + C2 \quad \text{(III)}$$

C1: proportional constant
C2: constant

Needless to say, when the concentration of the chemical substance is calculated on the basis of the voltage difference ΔE measured in the step (f), a calibration curve is used.

In other words, a plurality of the voltage differences ΔE are measured using a plurality of the sample solutions each containing the chemical substance at a different known concentration. On the basis of the plurality of the measured voltage differences ΔE and the concentrations of the chemical substance, a calibration curve is prepared. The calibration curve has a predetermined proportional constant C1 and a predetermined constant C2.

Next, using a sample solution containing the chemical substance at an unknown concentration, the voltage difference ΔE is measured. Using the calibration curve, the concentration of the chemical substance is calculated from the measured voltage difference $\Delta E$.

The formula (III) is equivalent to the following formula (IV):

(the concentration of the chemical substance)=$10^{\{(\Delta E-d)/e\}}$ (IV)

where d and e are constants.

(Embodiment 2)

The embodiment 2 is identical to the embodiment 1, except for the following items (A) and (B).

(A): In the step (b), the counter electrode 13, the first reference electrode 12, the first working electrode 11a, the second working electrode 11b and the gel-coated electrode 15 are brought into contact with the sample solution 16. The second reference electrode 14 is not brought into contact with the sample solution 16.

(B): Before the step (f), the second reference electrode 14 is brought into contact with the sample solution 16.

In the embodiment 2, the substrate 10 does not have to be used. The individual six electrodes 11-15 may be brought into contact with the sample solution 16 separately. Alternatively, the substrate 10 may comprise the counter electrode 13, the first reference electrode 12, the first working electrode 11a, the second working electrode 11b and the gel-coated electrode 15. This substrate 10 does not comprise the second reference electrode 14.

EXAMPLE

The following examples describe the present invention in more detail.

The example is composed of the example 1a, the example 1b, the example 1c, the example 1d and the example 1e.

Example 1a

The electrochemical measurement system shown in FIG. 1B was prepared. This measurement system comprised the substrate 10, the switch 17, the potentiostat 18 and a pH meter (not shown). The substrate 10 comprised the first working electrode 11a, the second working electrode 11b, the first reference electrode 12, the counter electrode 13, the second reference electrode 14 and the gel-coated electrode 15 shown in FIG. 3C and FIG. 3D. The potentiostat 18 was available from BAS Inc. under the trade name of "dual potentiostat ALS-832C". The pH meter was available from HORIBA Ltd. under the trade name of "F-72T".

The first working electrode 11a and the second working electrode 11b were comb-shaped electrodes each formed of gold covered with a self-assembled film composed of alkanethiol. These two comb-shaped electrodes were engaged alternately. The comb-shaped electrode had an electrode width of 2 micrometers. The interval between the comb-shaped electrodes, namely, the electrode interval, was 2 micrometers.

The first reference electrode 12 was a silver/silver chloride electrode. The counter electrode 13 was a palladium electrode. The second reference electrode 14 was a silver/silver chloride electrode, similarly to the first reference electrode 12.

(Preparation of the Gel-coated Electrode 15)

The gel-coated electrode 15 was prepared as below.

Polymethyl methacrylate (available from Wako Pure Chemical Industries, Ltd., average molecular weight: approximately 100,000, 50 milligrams) was dissolved in 1 milliliter of acetone in a sealed vessel, so as to prepare an acetone solution. During the preparation of the acetone solution, ultrasonic wave was applied to the acetone, and the acetone was cooled in ice.

1-butyl-3-methylimidazolium chloride was purchased as the standard electrolyte from Wako Pure Chemical Industries, Ltd. 1-Butyl-3-methylimidazolium bis(trifluoromethanesulfonyl)imide was purchased as the ionic liquid from Tokyo Chemical Industry Kogyo Co., Ltd.

The 1-butyl-3-methylimidazolium chloride was dissolved in the 1-butyl-3-methylimidazolium bis(trifluoromethanesulfonyl)imide to obtain a 1-butyl-3-methylimidazolium bis(trifluoromethanesulfonyl)imide solution (50 microliters, hereinafter referred to as an "imide solution") which contained the 1-butyl-3-methylimidazolium chloride having a concentration of 1 mM.

Then, the imide solution was added to the acetone solution, and the mixture was stirred well. In this way, a stock solution was prepared.

The stock solution having a volume of 1.5 microliters was dropped to the opening shown in FIG. 3D. In this way, the gel 34 was formed on the electrode body 31, which was composed of the portion of the electrically conductive plate 32b exposed at the bottom surface of the opening. In this example, the electrically conductive plate 32b formed of silver was formed on the insulating substrate 35. Each of the electrically conductive plate 32b and the insulating substrate 35 had an area of 105 mm². The material of the insulating layer 33 was epoxy resin. The opening was cylindrical. The opening had a cross-sectional area of approximately 0.07 mm².

Then, the sample solution 16 was dropped onto the substrate 10. In this way, as shown in FIG. 1B, the substrate 10 was covered with the sample solution 16.

The sample solution 16 contained chemical reagents shown in the following Table 1.

TABLE 1

| Chemical reagents | Concentration |
|---|---|
| NaCl | 137.0 mM |
| KCl | 2.7 mM |
| $Na_2HPO_4$ | 8.1 mM |
| $KH_2PO_4$ | 1.5 mM |
| Human serum albumin | 10.0 mg/ml |
| Ferrocene-labeled anti-human serum albumin antibody | $1 \times 10^{-8}$M |

The switch 17 was turned on to apply the voltage V1 of 0.3 volts and the voltage V2 of 0 volts (vs. the first reference electrode 12) to the first working electrode 11a and the second working electrode 11b, respectively, for 60 seconds. The voltage V2 was also applied to the gel-coated electrode 15.

In this way, the chemical reaction represented by the following Chem 1 was developed on the first working electrode 11a.

[Chem 1]

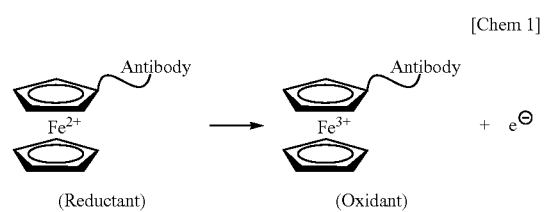

(Reductant) (Oxidant)

The chemical reaction represented by the following Chem 2 was developed on the second working electrode 11b.

[Chem 2]

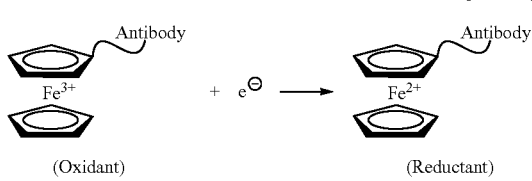

Then, the switch 17 was turned off.

The sample solution 16 was left as it stood for 180 seconds. When the 180 seconds had elapsed, as shown in FIG. 2B, the voltage difference ΔE between the second working electrode 11b and the second reference electrode 14 was measured with the voltmeter 19. The results are shown in Table 2 as the voltage difference ΔE measured for the first time. Meanwhile, the voltage of the first working electrode 11a was maintained at 0.3 volts.

The example 1a was repeated and the voltage difference ΔE was measured again. The results are shown in Table 2 as the voltage difference ΔE measured for the second time.

Example 1b

The experiment similar to the example 1a was performed, except that the concentration of the ferrocene-labeled anti-human serum albumin antibody was $1\times10^{-9}$ M.

Example 1c

The experiment similar to the example 1a was performed, except that the concentration of the ferrocene-labeled anti-human serum albumin antibody was $1\times10^{-10}$ M.

Example 1d

The experiment similar to the example 1a was performed, except that the concentration of the ferrocene-labeled anti-human serum albumin antibody was $1\times10^{-11}$ M.

Example 1e

The experiment similar to the example 1a was performed, except that the concentration of the ferrocene-labeled anti-human serum albumin antibody was $1\times10^{-12}$ M.

TABLE 2

| Concentration of the ferrocene-labeled anti-human serum albumin antibody | Voltage difference ΔE measured for the first time | Voltage difference ΔE measured for the second time | Average of Voltage difference ΔE |
|---|---|---|---|
| Example 1a | $1\times10^{-8}$M | 34.4 mV | 34.0 mV | 34.2 mV |
| Example 1b | $1\times10^{-9}$M | 19.7 mV | 22.4 mV | 21.1 mV |
| Example 1c | $1\times10^{-10}$M | 9.8 mV | 16.0 mV | 12.9 mV |
| Example 1d | $1\times10^{-11}$M | 8.6 mV | 13.7 mV | 11.2 mV |
| Example 1e | $1\times10^{-12}$M | 8.3 mV | 4.2 mV | 6.3 mV |

Figure 4:
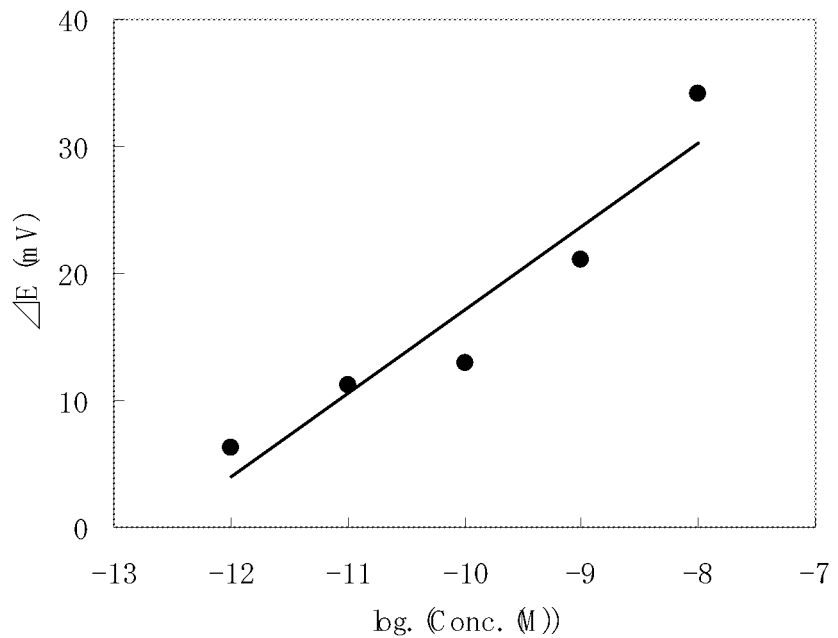
FIG. 4 is a graph showing the result of the example 1.

FIG. 4 is a graph showing the relationship between the average of the voltage difference ΔE and the concentration of the ferrocene-labeled anti-human serum albumin antibody. As is clear from FIG. 4, the average of the voltage difference ΔE is proportional to the common logarithm of the concentration of the ferrocene-labeled anti-human serum albumin antibody. In the example 1, the following formula was satisfied.

Average of the voltage difference $\Delta E = 6.58 \cdot \log_{10}$(the concentration of the antibody)+82.91

Accordingly, the graph shown in FIG. 4 can be served as a calibration curve. Using this calibration curve, the chemical substance contained in the sample solution at a significantly low concentration of not more than $1\times10^{-8}$M is quantified accurately using the oxidation-reduction substance (e.g., ferrocene derivative). In other words, the concentration of the chemical substance is measured accurately with use of the method according to the present invention, when the chemical substance is predicted to be contained in the sample solution at a significantly low concentration of not more than $1\times10^{-8}$M, however, the accurate concentration is unknown.

If the method according to the present invention has not discovered, it would be difficult for a skilled person to measure accurately the concentration of the chemical substance contained in the sample solution at a significantly low concentration of not more than $1\times10^{-8}$M.

The present invention provides a method for accurately quantifying the chemical substance contained in the sample solution at a significantly low concentration of not more than $1\times10^{-8}$M.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

The invention claimed is:

1. A method for accurately quantifying a chemical substance contained in a sample solution at a significantly low concentration of not more than $1\times10^{-8}$M, the method comprising steps of:
   (a) preparing a measurement system including a counter electrode, a first reference electrode, a first working electrode, a second working electrode, a second reference electrode and a gel-coated electrode; wherein
   the gel-coated electrode is electrically equivalent to the second working electrode;
   the gel-coated electrode comprises an electrode body and a gel;
   the surface of the electrode body is coated with the gel;
   the gel contains a standard electrolyte and an ionic liquid;
   the gel contains no water;
   the ionic liquid is hydrophobic and nonvolatile;
   the ionic liquid is composed of a cation and an anion; and
   the standard electrolyte is composed of the cation selected from the following Group (I) and a halide ion selected from the group consisting of a chloride ion, a bromide ion and an iodide ion;
   Group (I): cations represented by the following formulae IV-(1) to IV-(6):

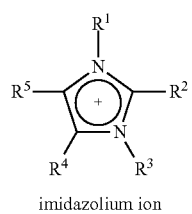

IV-(1)

imidazolium ion

17

-continued

IV-(2)

isoquinolium ion

IV-(3)

pyridinium ion

IV-(4)

pyrrolidinium ion

IV-(5)

piperidinium ion

IV-(6)

ammonium ion where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may include a heteroatom, an aralkyl group, or an aryl group;

(b) bringing the counter electrode, the first reference electrode, the first working electrode, the second working electrode, the second reference electrode and the gel-coated electrode into contact with the sample solution; wherein the sample solution contains the chemical substance and an oxidation-reduction substance or contains the chemical substance modified with an oxidation-reduction substance;

(c) applying voltages of V1 volts and V2 volts (V1>V2) to the first working electrode and the second working electrode, respectively, for a first predetermined period t1 with use of a potentiostat so as to develop chemical

18 reactions represented by the following chemical formulae (I) and (II) on the surfaces of the first working electrode and the second working electrode, respectively;

on the first working electrode:

$$\left[\begin{array}{c}\text{the} \\ \text{oxidation-} \\ \text{reduction} \\ \text{substance}\end{array}\right]^{n\oplus} \longrightarrow \left[\begin{array}{c}\text{the} \\ \text{oxidation-} \\ \text{reduction} \\ \text{substance}\end{array}\right]^{(n+m)\oplus} + me^{\ominus} \quad (I)$$

(reductant) (oxidant)

where, n represents an integer, and m represents a positive integer;

on the second working electrode:

$$\left[\begin{array}{c}\text{the} \\ \text{oxidation-} \\ \text{reduction} \\ \text{substance}\end{array}\right]^{(n+m)\oplus} + me^{\ominus} \longrightarrow \left[\begin{array}{c}\text{the} \\ \text{oxidation-} \\ \text{reduction} \\ \text{substance}\end{array}\right]^{n\oplus} \quad (II)$$

(oxidant) (reductant)

where, n represents an integer, and m represents a positive integer;

(d) stopping the application of the voltage to the second working electrode and the gel-coated electrode, when the first predetermined period t1 elapses;

(e) leaving the sample solution as it stands for a second predetermined period t2 after the step (d);

(f) measuring a voltage difference ΔE between the second working electrode=and the second reference electrode after the step (e); and (g) calculating a concentration of the chemical substance on the basis of the following formula (III):

$$\Delta E = C1 \cdot \log_{10}(\text{the concentration of the chemical substance}) + C2 \quad (III)$$

C1: proportional constant
C2: constant.

2. The method according to claim 1, wherein the voltage difference between the voltages of V1 and V2 in the step (c) is not less than 0.3 volts and not more than 0.6 volts.

3. The method according to claim 1, wherein the first predetermined period t1 is not less than 10 seconds and not more than 600 seconds.

4. The method according to claim 1, wherein the second predetermined period t2 is not less than 10 seconds and not more than 600 seconds.

5. The method according to claim 1, wherein the oxidation-reduction substance is a ferrocene derivative.

6. The method according to claim 5, wherein the ferrocene derivative is ferrocenecarboxylic acid.

7. The method according to claim 1, wherein the chemical substance is an antibody.

8. The method according to claim 1, wherein,
the cation and the anion of the ionic liquid are selected from the following groups (I) and (II), respectively:

Group (I): cations represented by the following formulae IV-(1) to IV-(6):

IV-(1)

imidazolium ion

IV-(2)

isoquinolium ion

IV-(3)

pyridinium ion

IV-(4)

pyrrolidinium ion

IV-(5)

piperidinium ion

IV-(6)

ammonium ion where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may include a heteroatom, an aralkyl group, or an aryl group;

Group (II): anions represented by the following formula V-(1) and V-(2):

V-(1)

V-(2)

where $Rf^1$ and $Rf^2$ are the same as or different from each other, and each represents a perfluoroalkyl group having carbon number of 1 to 4.

9. The method according to claim 1, wherein,
the ionic liquid is selected from the following:
1,3-dimethylimidazolium bis(trifluoromethanesulfonyl)imide,
1-ethyl-3-methylimidazolium bis(trifluoromethanesulfonyl)imide,
1-ethyl-3-methylimidazolium triflate,
1-ethyl-3-methylimidazolium bis(pentafluoroethanesulfonyl)imide,
1,3-diethylimidazolium bis(trifluoromethanesulfonyl)imide,
1,3-diethylimidazolium triflate,
1-butyl-3-ethylimidazolium triflate,
1,2-dimethyl-3-ethylimidazolium bis(trifluoromethanesulfonyl)imide,
1-butyl-3-methylimidazolium bis(trifluoromethanesulfonyl)imide,
1-butyl-3-methylimidazolium triflate,
1-isopropyl-3-methylimidazolium bis(trifluoromethanesulfonyl)imide,
1,2-dimethyl-3-propylimidazolium bis(trifluoromethanesulfonyl)imide,
N,N-propylmethylpyrrolidinium bis(trifluoromethanesulfonyl)imide,
propyltrimethyammonium bis(trifluoromethanesulfonyl)imide,
N,N-methylpropylpiperidinium bis(trifluoromethanesulfonyl)imide, or
N-butylpyridinium bis(trifluoromethanesulfonyl)imide.

10. A method for accurately quantifying a chemical substance contained in a sample solution at a significantly low concentration of not more than $1 \times 10^{-8}$M, the method comprising steps of:
(a) preparing a measurement system including a counter electrode, a first reference electrode, a first working electrode, a second working electrode, a second reference electrode and a gel-coated electrode; wherein
the gel-coated electrode is electrically equivalent to the second working electrode;
the gel-coated electrode comprises an electrode body and a gel;
the surface of the electrode body is coated with the gel;
the gel contains a standard electrolyte and an ionic liquid;
the gel contains no water;
the ionic liquid is hydrophobic and nonvolatile;
the ionic liquid is composed of a cation and an anion; and
the standard electrolyte is composed of the cation selected from the following Group (I) and a halide ion selected from the group consisting of a chloride ion, a bromide ion and an iodide ion;

Group (I): cations represented by the following formulae IV-(1) to IV-(6):

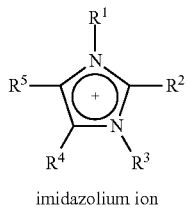

imidazolium ion

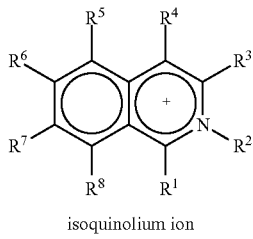

isoquinolium ion

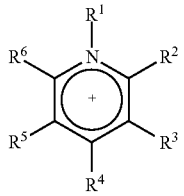

pyridinium ion

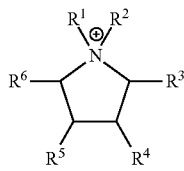

pyrrolidinium ion

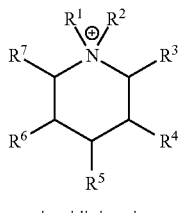

piperidinium ion

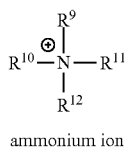

ammonium ion where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may include a heteroatom, an aralkyl group, or an aryl group;

(b) bringing the counter electrode, the first reference electrode, the first working electrode, the second working electrode and the gel-coated electrode into contact with the sample solution; wherein the sample solution contains the chemical substance and an oxidation-reduction substance or contains the chemical substance modified with an oxidation-reduction substance; and the second reference electrode is not in contact with the sample solution;

(c) applying voltages of V1 volts and V2 volts (V1>V2) to the first working electrode and the second working electrode, respectively, for a first predetermined period t1 with use of a potentiostat so as to develop chemical reactions represented by the following chemical formulae (I) and (II) on the surfaces of the first working electrode and the second working electrode, respectively;

on the first working electrode:

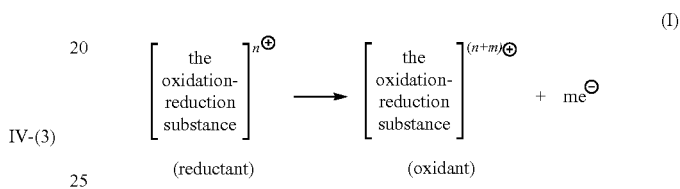

where, n represents an integer, and m represents a positive integer;

on the second working electrode:

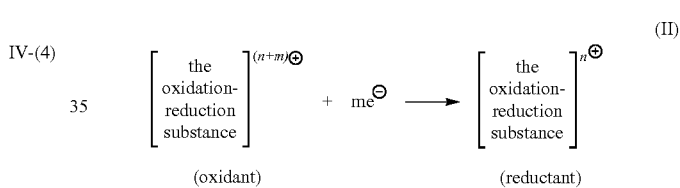

where, n represents an integer, and m represents a positive integer;

(d) stopping the application of the voltage to the second working electrode and the gel-coated electrode when the first predetermined period t1 elapses;

(e) leaving the sample solution as it stands for a second predetermined period t2 after the step (d);

(f) bringing the second reference electrode into contact with the sample solution;

(g) measuring a voltage difference $\Delta E$ between the second working electrode and the second reference electrode after the step (f); and (h) calculating a concentration of the chemical substance on the basis of the following formula (III):

$$\Delta E = C1 \cdot \log_{10}(\text{the concentration of the chemical substance}) + C2 \quad \text{(III)}$$

C1: proportional constant
C2: constant.

11. The method according to claim 10, wherein the voltage difference between the voltages of V1 and V2 in the step (c) is not less than 0.3 volts and not more than 0.6 volts.

12. The method according to claim 10, wherein the first predetermined period t1 is not less than 10 seconds and not more than 600 seconds.

13. The method according to claim 10, wherein the second predetermined period t2 is not less than 10 seconds and not more than 600 seconds.

14. The method according to claim 10, wherein the oxidation-reduction substance is a ferrocene derivative.

15. The method according to claim 14, wherein the ferrocene derivative is ferrocenecarboxylic acid.

16. The method according to claim 10, wherein the chemical substance is an antibody.

17. The method according to claim 10, wherein, the cation and the anion of the ionic liquid are selected from the following groups (I) and (II), respectively:

Group (I): cations represented by the following formulae IV-(1) to IV-(6):

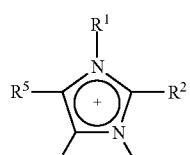

imidazolium ion IV-(1)

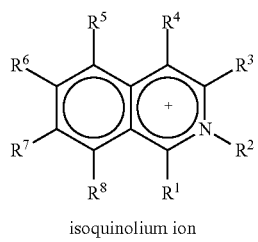

isoquinolium ion IV-(2)

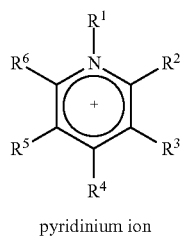

pyridinium ion IV-(3)

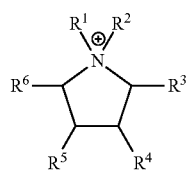

pyrrolidinium ion IV-(4)

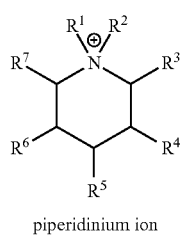

piperidinium ion IV-(5)

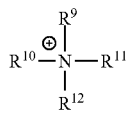

ammonium ion IV-(6)

where $R^1$, $R^2$, $R^3$, $R^4$, $R^5$, $R^6$, $R^7$, and $R^8$ are the same as or different from each other, and each represents a hydrogen atom, a straight or branched alkyl group which may include a heteroatom, an aralkyl group, or an aryl group, and $R^9$, $R^{10}$, $R^{11}$, and $R^{12}$ are the same as or different from each other, and each represents a straight or branched alkyl group which may include a heteroatom, an aralkyl group, or an aryl group;

Group (II): anions represented by the following formulae V-(1) and V-(2);

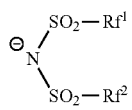

V-(1)

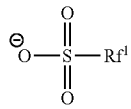

V-(2)

where $Rf^1$ and $Rf^2$ are the same as or different from each other, and each represents a perfluoroalkyl group having carbon number of 1 to 4.

18. The method according to claim 10, wherein,
the ionic liquid is selected from the following:
1,3-dimethylimidazolium bis(trifluoromethanesulfonyl)imide,
1-ethyl-3-methylimidazolium bis(trifluoromethanesulfonyl)imide,
1-ethyl-3-methylimidazolium triflate,
1-ethyl-3-methylimidazolium bis(pentafluoroethanesulfonyl)imide,
1,3-diethylimidazolium bis(trifluoromethanesulfonyl)imide,
1,3-diethylimidazolium triflate,
1-butyl-3-ethylimidazolium triflate,
1,2-dimethyl-3-ethylimidazolium bis(trifluoromethanesulfonyl)imide,
1-butyl-3-methylimidazolium bis(trifluoromethanesulfonyl)imide,
1-butyl-3-methylimidazolium triflate,
1-isopropyl-3-methylimidazolium bis(trifluoromethanesulfonyl)imide,
1,2-dimethyl-3-propylimidazolium bis(trifluoromethanesulfonyl)imide,
N,N-propylmethylpyrrolidinium bis(trifluoromethanesulfonyl)imide,
propyltrimethyammonium bis(trifluoromethanesulfonyl)imide,
N,N-methylpropylpiperidinium bis(trifluoromethanesulfonyl)imide, or
N-butylpyridinium bis(trifluoromethanesulfonyl)imide.

* * * * *